United States Patent
Wu

(10) Patent No.: US 7,166,234 B1
(45) Date of Patent: *Jan. 23, 2007

(54) DIALDEHYDE ASSAY

(75) Inventor: Wen H. Wu, Elkhart, IN (US)

(73) Assignee: Integrated Biomedical Technology, Inc., Elkhart, IN (US)

(*) Notice: Subject to any disclaimer, the term of this patent is extended or adjusted under 35 U.S.C. 154(b) by 1106 days.

This patent is subject to a terminal disclaimer.

(21) Appl. No.: 09/697,374

(22) Filed: Oct. 26, 2000

(51) Int. Cl.
*C09K 5/16* (2006.01)

(52) U.S. Cl. .......................................... 252/1
(58) Field of Classification Search .................. 252/1
See application file for complete search history.

(56) References Cited

U.S. PATENT DOCUMENTS

| | | | | |
|---|---|---|---|---|
| 4,328,182 A | | 5/1982 | Blake | 422/56 |
| 4,521,376 A | | 6/1985 | Witonsky et al. | 422/56 |
| 4,643,980 A | | 2/1987 | Witonsky et al. | 436/128 |
| 4,902,719 A | * | 2/1990 | Gerhart et al. | 514/564 |
| 4,937,234 A | * | 6/1990 | Fahim | 514/53 |
| 5,370,865 A | * | 12/1994 | Yamagishi et al. | 424/54 |
| 5,380,533 A | * | 1/1995 | Egidio et al. | 424/456 |
| 5,464,775 A | | 11/1995 | Smith | 436/63 |
| 5,603,923 A | * | 2/1997 | Robinson et al. | 424/60 |
| 6,436,716 B1 | * | 8/2002 | Wu | 436/128 |

OTHER PUBLICATIONS

Lynch, Evaluation of the efficacy and safety of sporicidin-HD and formaldehyde in reprocessed dialyzers: a comparative study, *Hemodialyzer Reuse: Issues and Solutions*, pp. 154-159, 1985.
Wendt et al., Safety, efficacy, and performance of CIDEX dialyzer disinfectant for reprocessing hemodialyzers, *Hemodialyzer Reuse: Issues and Solutions*, pp. 160-165, 1985.
Product Brochure, *Ultrafast* Nephretect, Formaldehyde & Glutaraldehyde Test Reagent, (Oct. 16, 1996).
Product insert, Serim Formaldehyde Test Strips (Feb. 1998).
Product insert, Maxi-Strip, Dialdehyde Concentration Indicator, Undated.
Product insert, Cidexplus, Undated.
Product insert, CIDEX* Family of Solutions Test Strips (1994).
Product insert, Serim Disintek XL Test Strips (Jun. 2000).
Serim Research Corp. website (Sep. 14, 2000—printed).
Product insert, MaxiCide, Undated.
Product insert, MaxiCide Plus, Undated.
Material safety data sheet, label, and product insert WAVICIDE-01 (1998).
Product insert and container, Cidexplus, Undated.
Product insert and container, Cidex, Undated.
"Safe use and handling of glutaraldehyde-based products in health care facilities," American National Standard, ANSI/AAMI ST58 (1996).
Product insert, Omnicide® 28, Undated.
J. Frederic Walker, *Formaldehyde*, 3rd ed., Reinhold Publishing Corporation, NY, NY (1964), Chapters 14 (pp. 359-414), 17 (pp. 467-482), and 18 (pp. 483-510).
Brochure, Reuse of hemodialyzers, *Association for the Advancement of Medical Instrumentation*, ANSI/AAMI RD47, pp. 1-26 1993.
Brochure, Hemodialyzer reuse: Issues and solutions, *AAMI Analysis and Review*, TAR No. 10-85, pp. 135-139, 141-143, 145-153 (1985).

* cited by examiner

*Primary Examiner*—Monique T. Cole
(74) *Attorney, Agent, or Firm*—Marshall, Gerstein & Borun LLP

(57) ABSTRACT

A composition, method, and device for quantitatively determining the concentration of a dialdehyde in a sample are disclosed. The device includes a test pad having a suitable carrier matrix incorporating an indicator reagent composition capable of interacting with a dialdehyde to produce a detectable and measurable response for dialdehyde concentration over a range of 0% to about 20%, by weight of the sample. An indicator reagent composition contains: (a) a diamino carboxylic acid, (b) an optional polymer and (c) a carrier. An indicator reagent composition is incorporated into a carrier matrix to provide a test pad useful in a dry phase dialdehyde assay of a sample, especially for samples containing a high concentration of glutaraldehyde.

14 Claims, No Drawings

DIALDEHYDE ASSAY

FIELD OF THE INVENTION

The present invention relates to a composition, method, and device for determining the concentration of a dialdehyde in a sample. More particularly, the present invention relates to a method and device for assaying an aqueous sample for a dialdehyde concentration of 0% to about 20%, by weight, by using an improved indicator reagent composition. Contrary to prior compositions, the present indicator reagent compositions have the advantage of quantitatively measuring a high range of dialdehyde concentration in a sample without requiring multistep titration procedures. The invention is particularly effective for determining the concentration of glutaraldehyde.

BACKGROUND OF THE INVENTION

Aldehydes have been used for many years in the medical sciences for various purposes. It is well known, for example, that formaldehyde and glutaraldehyde are useful for fixing and preserving tissue specimens. In recent years, the role of aldehydes in the medical community has expanded to that of a germicide useful for disinfecting or sterilizing medical instruments.

Glutaraldehyde is a commonly used dialdehyde in the medical industry. Typically, glutaraldehyde is used as a germicide for disinfection of reusable medical devices, such as surgical instruments or endoscopes. The effective level of glutaraldehyde in commercial disinfection solutions generally ranges from about 1.5% to 3.5%, by weight of the solution. For example, CIDEX® 14 Day solution contains 2.4% glutaraldehyde as the active ingredient, and CIDEX® 28 Day solution contains 3.5% glutaraldehyde as the active ingredient.

The effectiveness of the germicidal solution is related to the concentration of the aldehyde. The monitoring of the aldehyde levels in the germicide solution is particularly important in assuring the effectiveness of the disinfectant. Unfortunately, presently available aldehyde assay procedures generally either lack accurate quantification or involve complicated sample preparation, which reduces the convenience and efficiency of the assay.

For example, U.S. Pat. Nos. 4,521,376 and 4,643,980 disclose a test system for glutaraldehyde consisting of a mixture having a defined ratio of sodium sulfite and an amine compound, in particular the amino acid glycine. The sodium sulfite and the amino acid react with glutaraldehyde to form a yellow-colored complex. In practice, the commercial product utilizing the principles described in U.S. Pat. Nos. 4,521,376 and 4,643,980 involves a three-step reaction. First, glutaraldehyde is reacted with sodium sulfite to form a sulfite addition product and sodium hydroxide. Second, sodium hydroxide reacts with glycine to form sodium glycinate. Third, sodium glycinate reacts with another molecule of glutaraldehyde to form a yellow-colored addition product. The test strips based on this chemical sequence are "semi-quantitative" chemical indicators for use in determining whether the concentration of glutaraldehyde is above or below an established minimum concentration for a solution. The test strips are commercially available as the CIDEX® family of solutions test strips (Johnson & Johnson Medical, Inc., Arlington, Tex., U.S.A.).

The "semi-quantitative" test strip is a qualitative threshold test to determine whether the concentration of glutaraldehyde in a given sample meets a designated threshold. The test serves to indicate, either positively or negatively, whether the disinfectant solution contains a required minimum effective level of glutaraldehyde. A sample that contains the threshold level changes the color of the strip to yellow, indicating that the sample passes the assay. If the sample does not contain the threshold level of glutaraldehyde, the strip does not undergo a color transition, indicating that the sample fails the assay. The test does not provide a continuous quantitative assay of glutaraldehyde levels in the solution.

Moreover, the reaction described in U.S. Pat. Nos. 4,521,376 and 4,643,980 requires the use of both the sulfite and the amine compound to afford the desired color response. Neither patent discloses that an amino acid alone can form a chromophore, permitting quantification of an amount of aldehyde, particularly glutaraldehyde. In addition, neither patent discloses use of a diamino carboxylic acid in any assay, either quantitative or qualtitative, for aldehydes, including dialdehydes.

Sodium sulfite and bisulfite methods as well as reactions with organic nitrogen containing compounds have been described for quantitative assay of aldehydes, but typically formaldehyde. These methods are tedious, and require a multistep titration to afford an accurate result. In addition, these reactions can generate strong base, such as sodium hydroxide, in sulfite/bisulfite methods, or, in the case of nitrogen containing compounds, the compounds, for example amino acids, can react as strong acids. The accurate quantitation of the strong acidic or basic component of the reaction is neither convenient nor feasible for a dry reagent test strip. A more thorough description of the sodium sulfite and sodium bisulfite methods can be found in J. F. Walker, "Quantitative Analysis of Formaldehyde," in *Formaldehyde*, 3rd ed., Reinhold Publishing Corporation, New York, N.Y., pp. 486–488 (1964). Further description of the reaction of formaldehyde with organic nitrogen containing compounds, and more particularly amino acids, can be found in J. F. Walker, "Reaction with Amines, Amides and Nitriles," in *Formaldehyde*, 3rd ed., Reinhold Publishing Corporation, New York, N.Y., pp. 359–414, in particular pp. 395–398 (1964).

Other assays typically employed for detecting glutaraldehyde use chromogenic reactions to form a colored adduct, such as described in U.S. Pat. No. 5,464,775. These reactions generally are used in a solution format assay for detecting glutaraldehyde in adult urine samples as evidence of urine adulteration. The assays require a chromogenic reaction of the aldehyde in a test sample with an aqueous carbonyl indicator, typically an aromatic azine or azide. These compounds are capable of forming a detectable chromogenic adduct. Examples of such indicator reagents named in U.S. Pat. No. 5,464,775 include, for example, 2,4-dinitrophenyl hydrazine, 4-nitrophenyl hydrazine, hydrazine, phenylhydrazine, semicarbazide hydrochloride, and hydroxylamine. Generally, these compounds have conjugated or aromatic systems that allow for color formation.

To date, no known single assay is available to quantitatively assay aldehyde concentrations based on the formation of a colored chromophore in an efficient, effective manner. Accordingly, it would be beneficial to provide an assay to analyze a test sample for aldehyde concentration, particularly glutaraldehyde concentration, in a simple, convenient dry test strip or solution format for detecting liquid or gaseous aldehyde concentration.

SUMMARY OF THE INVENTION

The present invention is directed to providing a composition for measuring a dialdehyde concentration of 0% to about 20%, and especially about 0.5% to about 6%, by weight, without requiring titration or inefficient sample handling. The present invention is directed to an assay method and device that can be used to assay a test sample containing 0% to about 20%, by weight, or more, of a dialdehyde. In the present invention, one or more diamino carboxylic acids can be used to provide an accurate and wide detection range with a continuous color response from 0% to about 20%, by weight, dialdehyde.

The present method of assaying for dialdehyde content in a test sample yields trustworthy and reproducible results by utilizing an indicator reagent composition that undergoes a color transition in response to dialdehyde concentration. Additionally, the method and composition utilized in the assay does not adversely affect or interfere with any other test reagent pads that are present on a multiple test pad strip.

In accordance with the present invention, an indicator reagent composition can be incorporated into a carrier matrix to provide sufficient sensitivity and color differentiation to assay for dialdehyde concentration over the range of 0% to about 20%, and particularly about 0.5% to about 6%, by weight, without requiring titration or inefficient sample handling.

The present invention provides a new and improved composition, device, and method of determining dialdehyde concentration in a test sample. A device includes a test pad comprising a suitable carrier matrix incorporating an indicator reagent composition capable of interacting with dialdehyde to produce a detectable response to dialdehyde concentration. A carrier matrix of the test pad comprises a bibulous material, such as filter paper; a nonbibulous material, such as a strip, layer, or membrane of a polymerized material; or a mixture thereof. An indicator reagent composition is homogenously incorporated into the carrier matrix, and the carrier matrix holds the indicator reagent composition homogeneously throughout the carrier matrix while maintaining the permeability of the carrier matrix to the sample.

More particularly, the present invention is directed to a method of assaying a dialdehyde content of an aqueous sample by utilizing a new indicator reagent composition. It has been demonstrated that a reagent composition including: (a) a diamino carboxylic acid, (b) an optional polymer, and (c) a carrier, for example water, affords excellent sensitivity to quantitatively assay a test sample for dialdehyde content. The assay provides a method of determining the concentration of the dialdehyde with sufficient color differentiation to quantitatively measure a dialdehyde concentration of 0% to about 20%, and particularly about 0.5% to about 6%, by weight, of the dialdehyde, particularly an aliphatic dialdehyde. The present invention most preferably is used to detect levels of $C_2$–$C_6$ aliphatic dialdehydes and, to achieve the full advantage of the present invention, to detect levels of glutaraldehyde.

An important feature of the present invention is to provide an accurate and reliable quantitative determination for a concentration of dialdehyde in a liquid, typically aqueous, or gaseous sample. The quantitative determination can be achieved in accordance with the invention by allowing a test sample containing a concentration of dialdehyde to interact with the indicator reagent composition. The indicator reagent composition responds to the dialdehyde content of the sample, even at a high concentration, to provide a differentiable color transition. Quantitative assay of the test samples is more sensitive and more accurate than achieved with previously disclosed compositions because the indicator reagent composition is able to detect and differentiate between high levels of dialdehyde present in the sample without titration or multistep sample handling.

Therefore, one aspect of the invention provides a method and composition for quantitatively determining the concentration of aqueous or gaseous dialdehyde. The composition interacts with the dialdehyde to produce a change in color of a device that is indicative of the concentration of the dialdehyde in the sample.

Another aspect of the invention is to provide a method of assaying a test sample containing a dialdehyde, said method having sufficient sensitivity and visual color resolution to allow differentiation between, and quantitative measurement of, samples having different concentrations of dialdehydes, including glutaraldehyde in particular.

Yet another aspect of the present invention is to provide a sensitive method of assaying samples for dialdehyde concentration of 0% to about 20%, by weight, dialdehyde. The present method is especially useful in the detection of a high concentration of dialdehyde, e.g., about 0.5% to greater than about 6% by weight of the sample.

Another aspect of the present invention is to provide an indicator reagent composition that interacts with a dialdehyde, and undergoes a visually or instrumentally differentiable color transition to allow determination of the dialdehyde concentration in the sample.

Another aspect of the present invention is to provide a method of assaying the dialdehyde content of a sample by incorporating an indicator reagent composition into a dry phase detection device, wherein the indicator reagent composition comprises: (a) a diamino carboxylic acid, (b) an optional polymer, preferably a cellulose-based polymer, and (c) a carrier, such as water.

Still another aspect of the present invention is to provide a new and improved method of determining the dialdehyde content of an aqueous sample by utilizing a test device, including a carrier matrix, said carrier matrix comprising a bibulous matrix, like filter paper, or a nonbibulous matrix, like a glass fiber or a layer of a permeable polymeric material, and said carrier matrix having incorporated therein an indicator reagent composition capable of interacting with a dialdehyde present in the sample, to provide a color transition that can be correlated to the concentration of the dialdehyde in the sample.

A further aspect of the present invention is to provide an improved dry phase test strip that incorporates an indicator reagent composition comprising (a) a diamino carboxylic acid, and (b) an optional polymer, and thereby provide a quantitative assay for the dialdehyde content in a sample.

Yet another aspect of the present invention provides a solution form of assay comprising (a) contacting a diamino carboxylic acid with a sample potentially containing a dialdehyde, (b) allowing the diamino carboxylic acid to react with any dialdehyde present in the sample, and (c) detecting a change in color or absorbance of the sample.

Still another aspect of the present invention is to provide an assay of a gaseous or vapor sample for dialdehyde content. The assay comprises the steps of (a) incorporating an indicator reagent composition comprising (i) a diamino carboxylic acid, and (ii) an optional polymer into a carrier matrix, and (b) exposing the indicator reagent composition to a gaseous sample potentially containing the dialdehyde.

The above and other aspects, advantages, and novel features of the present invention will become apparent from the following detailed description of the invention.

DETAILED DESCRIPTION OF THE PREFERRED EMBODIMENTS

In accordance with the method of the present invention, a quantitative assay of aqueous samples for dialdehyde content, and especially high concentrations of a dialdehyde, is accomplished by utilizing an indicator reagent composition that includes (a) a diamino carboxylic acid, (b) an optional polymer, and (c) a carrier. By employing an indicator reagent composition of the present invention, sufficient sensitivity and sufficient visual color differentiation between samples of different dialdehyde content is achieved. In accordance with the method of the present invention, samples having a dialdehyde content of 0% to about 20%, and particularly about 0.5% to about 6%, by weight of the sample, can be measured and differentiated.

To achieve the full advantage of the present invention, the method and composition are employed in dry phase, test pad assays to determine the concentration of a dialdehyde in an aqueous solution or, alternatively, a gaseous vapor. The dialdehyde commonly is a component of a germicide solution, for example a glutaraldehyde solution. A dry phase test strip, including a test pad comprising a carrier matrix incorporating an indicator reagent composition of the present invention, allows the rapid quantitative assay of samples by visual means.

In particular, the present invention allows determination of dialdehyde concentration of the sample by the visual color change of a test pad on a test strip resulting from contact between the test strip and the sample. The dialdehyde concentration of the sample is determined by correlating the detected color change to the dialdehyde concentration of the sample. The test strip includes a test pad comprising an inert carrier matrix incorporating an indicator reagent composition. The present method allows rapid calorimetric determination of the dialdehyde concentration of a sample, especially providing a suitable method for quantitatively measuring the concentration of the dialdehyde in aqueous solution.

Previous assay methods employed compositions that were unable to distinguish between aqueous solutions containing different concentrations of dialdehyde, particularly in the range of 1% to 2%, by weight. The prior compositions utilized end point indicators without varying color gradations, making discrimination between different concentrations of dialdehyde indistinguishable. In contrast, the present method detects the content of dialdehyde in the sample by utilizing an indicator reagent composition that provides varying colors corresponding to different concentrations of the dialdehyde in solution, thereby improving the overall quantifiable range of the dialdehyde.

The diamino carboxylic acid utilized in the present indicator reagent composition typically is a lower (i.e., $C_2$–$C_6$) carboxylic acid containing at least two amino groups and having a slightly acidic to neutral pH when dissociated in water. In preferred embodiments, the diamino carboxylic acid is represented by the general formula:

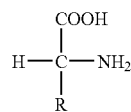

wherein R is alkyl substituted with amino, amido, guanidino, ureido, and further optionally substituted with hydroxy. Preferably, the alkyl group is a straight chain alkyl group containing from one to about four carbon atoms.

As used herein, the term "alkyl" refers to a straight- or branched-chain hydrocarbon group containing one to about six carbon atoms and, preferably one to about four carbon atoms, unless otherwise noted, which can be optionally substituted with one or more functional groups.

The term "amino" refers to a —$NH_2$ group.

The term "guanidino" refers to a —NH(C=NH)$NH_2$ group.

The term "hydroxy" refers to a —OH group.

Nonlimiting examples of diamino carboxylic acids suitable for the invention are lysine, ornithine, L-2,3-diaminopropionic acid, L-2,3-diaminobutyric acid, arginine, canavanine, hydroxylysine, asparagine, glutamine, and mixtures thereof. The preferred diamino carboxylic acids are lysine, ornithine, arginine, and mixtures thereof. The amount of a diamino carboxylic acid, either alone or in combination with the addition of other diamino carboxylic acids, in the present indicator reagent composition is about 1% to about 25%, by weight, and more preferably about 5% to about 15%, by weight of the composition.

The diamino carboxylic acids can react with dialdehydes, particularly aliphatic dialdehydes. The term "aliphatic dialdehyde" refers to a straight-chain hydrocarbon group containing two aldehyde (—CHO) groups. The hydrocarbon group typically contains two to ten, and preferably two to six, carbon atoms. Examples of dialdehydes that can be assayed by the present method include, but are not limited to, oxalaldehyde, malonaldehyde, succinaldehyde, glutaraldehyde, and adipaldehyde. Commercially available products containing such dialdehydes include, but are not limited to, GLYOXAL® (oxaldehyde), CIDEX® (glutaraldehyde), CIDEXPLUS® (glutaraldehyde), OMNICIDE® 28 (glutaraldehyde), MAXICIDE® (glutaraldehyde), QUART® (glutaraldehyde), and WAVICIDE®-01 (glutaraldehyde).

To illustrate properties of the diamino carboxylic acids, aqueous solutions of the diamino carboxylic acids (1% by weight) were prepared in a 2.5% glutaraldehyde solution containing 0.75 M sodium phosphate buffer. The pH of the solutions were adjusted to a pH of 8.0 with sodium hydroxide or hydrochloric acid. The absorbance of the solutions at 450 nm were taken after ten minutes with a spectrophotometer. For solutions having absorbance greater than 1.0, the solutions were diluted 10 or 20 times with water before the absorbance readings were taken. The absorbance of the test solutions are summarized below in Table 1.

TABLE 1

Color formulation of Diamino Carboxylic Acids Reacting with Glutaraldehyde

| Diamino Carboxylic Acid | Absorbance (at 450 nm) | Solution Color |
|---|---|---|
| Lysine | 12.80 | Dark Brown |
| Ornithine | 10.40 | Dark Brown |
| L-2,3-Diamino-propionic acid | 1.59 | Yellow Brown |

TABLE 1-continued

Color formulation of Diamino Carboxylic Acids
Reacting with Glutaraldehyde

| Diamino Carboxylic Acid | Absorbance (at 450 nm) | Solution Color |
| --- | --- | --- |
| L-2,3-Diamino-butyric acid | 0.06 | Yellow |
| Arginine | 1.49 | Yellow Brown |
| Canavanine | 0.48 | Yellow |
| Hydroxylysine | 5.85 | Brown |
| Asparagine | 1.45 | Yellow Brown |
| Glutamine | 4.60 | Brown |

The diamino carboxylic acids useful in the present invention can form color adducts, or complexes, having varying intensity. Some diamino carboxylic acids can provide a chromophore having a strong color intensity, as indicated by high absorbance value at 450 nm in Table 1, such as lysine, ornithine and hydroxylysine. Other diamino carboxylic acids afford chromophores having weaker color intensity which is indicated by a low absorbance value at 450 nm in Table 1, for example, L-2,3-diaminobutyric acid, canavine, asparagine, arginine, and L-2,3-diaminopropionic acid.

This feature of the present invention obviates diluting the test sample prior to assay. For example, a test sample having a low dialdehyde content can be assayed using a diamino carboxylic acid having a low or high absorbance, but preferably a larger absorbance in order to achieve a sufficient color transition. A sample containing a higher dialdehyde content also can be assayed using a diamino carboxylic acid having a low or a higher absorbance, but a low absorbance diamino carboxylic acid may be preferred to eliminate the need to dilute the test sample in order to obtain differentiable color transitions.

This also can be accomplished by increasing or decreasing the concentration of a diamino carboxylic acid. The amine functionality then can form a differentiable colored transition that is directly correlated to the amount of dialdehyde in the sample. In the case where the dialdehyde is glutaraldehyde, the preferred diamino carboxylic acids are lysine and ornithine, which have amino groups about the same distance apart as the aldehyde groups in glutaraldehyde.

One advantage of the present invention is that two or more diamino carboxylic acids can be combined to provide an indicator reagent composition that forms a colored chromophore of a desired intensity when reacted with the dialdehyde. For example, a diamino carboxylic acid having a high absorbance value, which thereby produces chromophores having intense color, can be combined with a diamino carboxylic acid having a weaker absorbance value to change the desired range for the intensity of the color response relative to the dialdehyde concentration. In this way, one skilled in the art can customize the indicator reagent composition to test a wide variety of dialdehyde concentrations. It is well within the skill of one in the art to vary the amount and identity the diamino carboxylic acids based on the properties, for example the absorbance, of the diamino carboxylic acids to provide a desired indicator reagent composition for the desired dialdehyde and range of dialdehyde concentrations.

The indicator reagent composition also can optionally contain a polymer. Preferably, the polymer is a neutral, nonionic polymer. The indicator reagent composition can contain a mixture of polymers to achieve a broad range quantitative assay, and particularly a high range quantitative assay for dialdehyde content. The preferred polymers are water-soluble, cellulose-based polymers. Other water-soluble polymers, such as polyvinylpyrrolidone, also can be used as the polymer in the present indicator reagent composition.

The water-soluble, cellulose-based polymers are derivatives of cellulose wherein hydroxy groups on the sugar moiety of cellulose are modified with a short chain alkyl (i.e., $C_1$–$C_4$), alkyl alcohol, or alkyl carboxylic acid. Examples of some common cellulose modifications are replacing a portion of the hydroxy groups with methyl, hydroxymethyl, hydroxyethyl, hydroxyethylmethyl, hydroxypropyl, hydroxypropylmethyl, or carboxymethyl groups, for example.

Examples of water-soluble cellulose-based polymers useful in the present invention include, but are not limited to, methylcellulose, hydroxymethylcellulose, hydroxyethylcellulose, hydroxyethylmethylcellulose, hydroxypropylcellulose, hydroxypropylmethylcellulose, carboxymethylcellulose and salts thereof, hydroxybutylcellulose, cellulose acetate, carboxymethylhydroxyethylcellulose, hydroxybutylmethylcellulose, and mixtures thereof.

In addition to cellulose-based polymers, other water-soluble polymers can be used in the method and composition of the present invention. Such water-soluble polymers are neutral, nonionic polymers, for example, polyvinylpyrrolidone, hydrolyzed polyvinylpyrrolidone, poly(vinyl alcohol), poly(vinyl acetate), vinyl acetate-vinyl alcohol copolymers, poly(methacrylamide), polyoxypropylenepolyoxyethylene block polymers having one of the following structures:

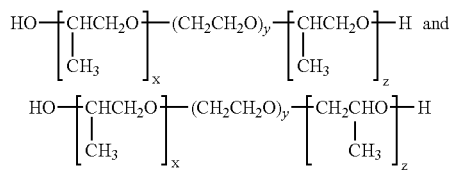

wherein x and z, independently, are an integer from about 4 to about 30, and y is an integer from about 4 to about 100, polyacrylamide, vinyl alcohol copolymers, and mixtures thereof.

The polymer is present in the indicator reagent composition in an amount of 0% to about 5%, and preferably about 0.1% to about 2.5%, by weight of the indicator reagent composition. To achieve the full advantage of the present invention, a water-soluble polymer is present in the indicator reagent composition in an amount of about 0.25% to about 0.75%, by weight of the composition.

The indicator reagent composition optionally can contain other chemically nonreactive ingredients. For example, one optional ingredient is a surfactant, in particular an anionic surfactant or a nonionic surfactant. The surfactant improves the ability of the sample to wet the carrier matrix, and the surfactant also improves the stability of the color transition of the indicator in response to the aldehyde.

The surfactant is present in the indicator reagent composition in an amount of 0% to about 1.5%, and preferably 0% to about 1%, by weight of the composition. To achieve the full advantage of the present invention, the surfactant is present in an amount of 0% to about 0.5% by weight of the composition.

Useful nonionic surfactants include, but are not limited to, an ethoxylated polysorbate, an ethoxylated alcohol, an ethoxylated phenol, i.e., an ethoxylated octylphenol, nonylphenol, or dodecylphenol with about 8 to about 30 moles of ethylene oxide, a polyethylene glycol, e.g., PEG-8 through PEG-40, a polypropylene glycol, e.g., PPG-9 through PPG-34, an ethylene glycol-propylene glycol copolymer, e.g., a poloxamer, and similar nonionic surfactants, and mixtures thereof. In general, a useful nonionic surfactant has an HLB value of about 6 to about 25.

Anionic surfactants useful in the present invention are not particularly limited. Usually, the anionic surfactant includes a hydrophobic moiety, such as a carbon chain including about eight carbon atoms to about 30 carbon atoms, and particularly about twelve carbon atoms to about twenty carbon atoms; and further includes a hydrophilic moiety, such as sulfate, sulfonate, carbonate, phosphate, or carboxylate. Often, the hydrophobic carbon chain is etherified, such as with ethylene oxide or propylene oxide, to impart a particular physical property or reduced surface tension, to the anionic surfactant.

The anionic surfactants are well known, and can be a fatty acid, a salt of a fatty acid, an ethoxylated fatty acid, or a salt of an ethoxylated fatty acid, for example. Therefore, suitable anionic surfactants include, but are not limited to, compounds in the classes known as alkyl sulfates, alkyl ether sulfates, alkyl ether sulfonates, sulfate esters of an alkylphenoxy polyoxyethylene ethanol, alpha-olefin sulfonates, beta-alkyloxy alkane sulfonates, alkyl arylsulfonates, alkyl carbonates, alkyl ether carboxylates, fatty acids, sulfosuccinates, alkyl ether sulfosuccinates, sarcosinates, octoxynol phosphates, nonoxynol phosphates, taurates, fatty taurides, sulfated monoglycerides, fatty acid amido polyoxyethylene sulfates, and isothienates; or mixtures thereof. Many additional anionic surfactants are described in *McCutcheon's, Detergents and Emulsifiers,* 1993 *Annual,* published by McCutcheon Division, MC Publishing Co., and incorporated herein by reference.

The alkyl sulfates and alkyl ether sulfates are particularly effective classes of anionic surfactants. Examples of anionic surfactants useful in the composition and method of the present invention include, but are not limited to, the ammonium, monoethanolamine, diethanolamine, triethanolamine, isopropylamine, sodium, potassium, lithium, or magnesium salt of lauryl sulfate, dodecylbenzenesulfonate, lauryl sulfosuccinate, lauryl ether sulfate, lauryl ether carboxylate, lauryl sarcosinate, cocomethyl tauride, and sulfosuccinate half ester amide; or mixtures thereof. Examples of especially useful anionic surfactants are a lauryl sulfate salt, a lauryl ether sulfate salt, a lauryl phosphate salt, a sulfosuccinate salt, a dodecylsulfonate salt, a cholate salt, a $C_8$ to $C_{18}$ fatty acid, and mixtures thereof.

The carrier for the ingredients of an indicator reagent composition includes water. However, organic solvents, such as acetone, methanol, ethanol, isopropyl alcohol, ethylene glycol, propylene glycol, dimethylformamide, dimethylsulfoxide, acetonitrile, ethyl acetate, and similar solvents, can be included in the carrier vehicle. The selection of a suitable organic solvent or solvents, in addition to water, to include in the carrier of the indicator reagent composition is within the capability of those skilled in the art of designing diagnostic assays.

The amount of organic solvent present in an indicator reagent composition generally is 0% to about 90%, and preferably about 10% to about 70%, by weight of the carrier. A carrier comprising water and an organic solvent, like methanol, ethanol, or acetone, is especially preferred because a carrier matrix impregnated with the indicator reagent composition can be dried within a few to several minutes.

The carrier matrix of the invention can be any substance capable of incorporating the chemical reagents required to perform the assay of interest, as long as the carrier matrix is substantially inert with respect to the chemical reagents. The carrier matrix also is porous or absorbent relative to the liquid sample.

The expression "carrier matrix" refers either to bibulous or nonbibulous matrices that are insoluble in the carrier of the indicator reagent composition and other physiological fluids and that maintain their structural integrity when exposed to the carrier and other physiological fluids. Suitable bibulous matrices include filter paper, sponge materials, cellulose, wood, woven and nonwoven fabrics, and the like. Nonbibulous matrices include glass fiber, polymeric films, and microporous membranes. Other suitable carrier matrices include hydrophilic inorganic powders, such as silica gel, alumina, diatomaceous earth and the like; argillaceous substances; cloth; hydrophilic natural polymeric materials, particularly cellulosic material, like cellulose beads, and especially fiber-containing papers such as filter paper or chromatographic paper; synthetic or modified naturally occurring polymers, such as cellulose acetate, polyvinyl chloride, polyacrylamide, polyacrylates, polyurethanes, crosslinked dextran, agarose, and other such crosslinked and noncrosslinked water-insoluble hydrophilic polymers. The carrier matrix can be of different chemical compositions or a mixture of chemical compositions. The matrix also can vary in regards to smoothness and roughness combined with hardness and softness. The handle usually is formed from hydrophobic materials such as cellulose acetate, polyethylene terephthalate, polycarbonate, or polystyrene. The carrier matrix is most advantageously constructed from filter paper or polymeric films.

The carrier matrix of the test strip can be any bibulous or nonbibulous material that allows permeation by the sample to saturate the test pad of the test strip that is impregnated with the indicator reagent composition. A preferred carrier matrix is a hydrophilic, bibulous matrix, including cellulosic materials, such as paper, and preferably filter paper. The carrier matrix also can be a hydrophilic, nonbibulous matrix, including polymeric films, such as a polyurethane or a crosslinked gelatin. Such polymeric films possess all of the qualities required of a carrier matrix of the present invention, including suspending and positioning both the essential ingredients and any optional ingredients included in the indicator reagent composition, and permeability of the sample through the carrier matrix.

The present invention can be used to assay an undiluted sample for dialdehyde concentration. As previously described, certain aldehydes, for example glutaraldehyde and formaldehyde, are commonly used to disinfect medical equipment, more particularly surgical instruments or endoscopes. Most indicator reagent compositions can only qualitatively assay an aldehyde or dialdehyde. The qualitative assays detect only the presence of the disinfecting agent, i.e., either glutaraldehyde and formaldehyde, relative to an established threshold level.

In contrast, the present invention can be used to assay undiluted samples for dialdehyde concentration over the range of 0% to about 20%, and especially about 0.5% to about 6%, by weight, of the composition. This capability greatly increases versatility of the invention because medical workers often use dialdehyde-containing germicide solutions to sanitize medical equipment. The effectiveness of the germicide solutions is directly dependent on the concentration of dialdehyde in the sample. The composition of the invention, therefore, can be used by medical personnel as a test for quantitatively identifying the amount of dialdehyde in a sample either as an aqueous solution or as a gaseous vapor.

The indicator reagent composition undergoes a color transition upon contact with the sample to provide an assay for dialdehyde concentration from the intensity and degree of the color transition. The indicator reagent composition of the present invention provides a sufficiently resolved and differentiated color transition such that the dialdehyde content in the sample can be measured and accurately determined without the use of color- or absorbance-measuring instruments, such as spectrophotometers or calorimeters, over a concentration range of 0% to about 20%, by weight of the composition.

The use of spectrophotometers and color-meters is particularly useful in a solution format of the test. In a solution-based assay, a liquid sample can be treated with the indicator reagent composition, typically in a carrier. The sample and indicator reagent composition are allowed to interact, forming a colored chromophore, which can be detected or analyzed with a calibrated calorimeter. Also, a spectrophotometer can be used to measure the absorbance of the treated sample. In the case of a solution containing glutaraldehyde, the reaction of glutaraldehyde with lysine or ornithine yield a color solution having a strong absorbance in the range of from about 300 nm to about 500 nm. Colorimetric or spectrophotometric data obtained from the treated sample can be compared with a standard curve constructed using solutions having known quantities of dialdehyde, for example glutaraldehyde.

Furthermore, the assay can be used to detect gaseous dialdehyde. In one example, the indicator reagent composition can be impregnated on reagent paper, i.e. filter paper, and used for the detection of glutaraldehyde in the air. The dialdehyde reacts with the indicator reagent composition causing a color change in the paper. The change in color can be compared with predetermined color gradations that correlate to known quantities of dialdehyde.

In another example, the impregnated reagent paper can be used as an indicator strip in a steam sterilization process. When a medical device is sterilized with dialdehyde vapor, such as glutaraldehyde, exposure to the vapor causes the reagent paper to change color. The color gradations can be compared to predetermined colors correlating to known quantities of dialdehyde in order to determine whether the dialdehyde content in the solution is sufficient for effective sterilization.

As previously described, the intensity and degree of the color transition are used to determine the dialdehyde content of the sample by comparing or correlating the color produced by the sample to colors produced by solutions having a known dialdehyde concentration. In accordance with an important feature of the present invention, the indicator reagent composition provides a sufficiently resolved and differentiated color transition such that the dialdehyde content of an undiluted sample can be measured for a dialdehyde content of 0% to about 20%, by weight, without requiring the use of color-measuring instruments.

An indicator reagent composition of the present invention, as described above, can be used in dry phase, test pad assays for dialdehyde. The dry phase, test pad assay for dialdehyde utilizing a present indicator reagent composition is performed in accordance with methods well known in the art. In general, the assay for dialdehyde is performed by contacting the sample with an indicator reagent composition, which typically is incorporated into an analyte detection device. In one method, the analyte detection device is contacted with an aqueous sample by dipping the analyte detection device into the aqueous sample. Alternatively, the aqueous sample can be applied to the analyte detection device dropwise. The resulting change in color of the analyte detection device reveals the dialdehyde concentration of the sample. If so designed, the resulting color transition can be compared to a standardized color chart to provide a measurement of the dialdehyde concentration of the sample.

The amount of dialdehyde also can be detected in a gaseous vapor, for example as a component of sterilizing steam treatment or as a vapor mix, such as a glutaraldehyde vapor in the air. To measure the dialdehyde content of the gaseous sample, the analyte detection device is directly exposed to the gaseous medium containing the dialdehyde by, for example, suspending the device in the medium.

Typically, the analyte detection device is a test strip impregnated with an indicator reagent composition, designed either as a single pad test strip (to assay only for a single analyte) or as a multiple pad test strip (to assay for several analytes simultaneously). For either type of test strip, the test strip includes a support strip, or handle, normally constructed from a hydrophobic plastic, and a reagent test pad, comprising a bibulous or nonbibulous carrier matrix. In general, the carrier matrix is an absorbent material that allows the liquid sample to move in response to capillary forces through the matrix to contact the indicator reagent composition and produce a detectable and measurable color transition.

In accordance with the method of the present invention, to perform a dry phase test strip assay for dialdehyde, an aqueous solution, including: (a) about 1% to about 25% by weight of a diamino carboxylic acid; (b) about 0% to about 5% by weight of a polymer, like a cellulose-based polymer; and (c) any other desired optional ingredients, or solvents, first is prepared. A nonbibulous matrix, such as a polyurethane film, or a bibulous matrix, such as filter paper, then is saturated or impregnated with the aqueous solution by immersing or by spraying the aqueous solution onto sheets or precut strips or pads of the polyurethane film or filter paper.

Then, after removing the aqueous solvent by drying in a forced air oven at a temperature of about 40° C. to about 100° C. for about 2 to about 15 minutes, the impregnated polyurethane film or filter paper, if necessary, is cut to an appropriate size, such as a pad having dimensions from about 0.2 in. (inch) (0.5 cm) by about 0.2 in (0.5 cm) to about 0.2 in. (0.5 cm) by about 1 in. (2.5 cm).

It should be understood that it is well within the experimental techniques of those skilled in the art of preparing test devices to determine the proper balance between size of the test pad, the strength of indicator reagent composition solutions, the amount of sample, and the method of introducing the sample to the test strip, such as by pipetting rather than dipping, in order to design a quantitative assay for dialdehyde content utilizing the method and composition of the present invention.

The dried, impregnated polyurethane film or filter paper then is secured to an opaque or transparent hydrophobic plastic handle with double-sided adhesive tape. The resulting test strip then is contacted with a sample for a sufficient time to saturate the test pad with the sample. After waiting a predetermined time, such as from about 60 to about 120 seconds, the test strip is examined, either visually or by instrument, for a response. The color transition, if any, of the test pad reveals the concentration of dialdehyde in the sample.

In many cases, simple visual observation of the test strip provides the desired information. If more accurate information is required, a color chart bearing color spots corresponding to various known concentrations of dialdehyde can be prepared for the particular indicator reagent composition used in the test strip. The resulting color of the test strip after contact with the sample then can be compared with the color spots on the chart to determine the concentration of dialdehyde in the sample. If a more accurate determination is required, a spectrophotometer or calorimeter can be used to more precisely determine the degree of the color transition. In addition, the dry phase test strip assay can be made quantitative by employing spectrophotometric or calorimetric techniques, as opposed to visual techniques, in order to more reliably and more accurately measure the degree of color transition, and, therefore, more accurately measure the concentration of dialdehyde in the sample.

In accordance with one embodiment of the present invention, the following dry phase test strips were prepared (1) to illustrate a test strip of the invention and (2) to demonstrate the effectiveness of the indicator reagent composition. All diamino carboxylic acids and reagents were purchased from Sigma-Aldrich (St. Louis, Mo., U.S.A.). Cellulose-based polymers were purchased from Aqualon Company (Wilmington, Del., U.S.A.).

EXAMPLE I

A 10% solution of DL-lysine free base was prepared with water. A water-soluble polymer, hydroxyethylcellulose, was prepared as a premixed 2.5% solution. The hydroxyethylcellulose solution was added to the reagent solution to obtain a final concentration of 0.25%, by weight, by replacing the equivalent volume of water. The final mixture of reagent solution was applied to filter paper, such as Schleicher & Schull #903 absorption paper, and immersed in a solution to impregnate solution components onto the paper. The impregnated filter was dried in a forced-air oven at 65° C. for 15 min. until the paper was dry. The dried reagent paper was assembled into a reagent strip by cutting the reagent paper into a 0.2 inch ribbon and adhering the paper to the long edge of a 2.5 inch wide polystyrene plastic sheet with a double sided adhesive. The reagent paper attached plastic sheet then was cut into 0.2 inch wide strips. The final strips had a 0.2×0.2 square inch reagent paper attached to a 0.2×2.5 plastic handle.

To test the color response of the reagent strip to various glutaraldehyde solutions, a stock solution of 25% glutaraldehyde, by weight, was diluted to 1, 2, 3, and 4%, by weight, respectively, with deionized water. The strips were dipped into the glutaraldehyde solution for one second, the excess solution was removed by touching the edge of the strip with a clean tissue paper. The strongest strip color response was obtained between 60 and 120 seconds. The color response of each impregnated strip is shown below in Table 2.

TABLE 2

Color response of reagent strips containing lysine-based indicator reagent composition for increasing glutaraldehyde concentration

| Glutaraldehyde Concentration | Color Response of Dry Reagent Strip |
|---|---|
| 1% | Yellow |
| 2% | Orange |
| 3% | Pumpkin |
| 4% | Reddish Brown |

EXAMPLE II

Dry reagent test strips were prepared with arginine and tested for color response to glutaraldehyde concentrations from 1 to 10%, by weight. The arginine-based reagent strips were prepared using similar procedures for preparing the above lysine-based reagent strips, but substituting arginine for lysine. A stock solution of 25% glutaraldehyde, by weight, was diluted with deionized water to concentrations of 1%, 3%, 5%, and 10%, by weight, to give a series of test solutions. The test solutions were tested with the prepared strips and the results are reported below in Table 3.

TABLE 3

Color response of reagent strips containing arginine-based indicator reagent composition for increasing glutaraldehyde concentration

| Glutaraldehyde Concentration | Color Response of Dry Reagent Strip |
|---|---|
| 1% | Yellow |
| 3% | Orange |
| 5% | Pumpkin |
| 10% | Reddish Brown |

The data in Tables 2 and 3 demonstrate an indicator reagent composition containing a diamino carboxylic acid provides a distinct color response for each different concentration of dialdehyde. More particularly, the data shows that an indicator reagent composition can be formulated containing one or more mixtures of different diamino carboxylic acids to provide a desired color response in the range of from about 0.5% to about 15%, by weight. In particular, the color transition was different for each concentration of glutaraldehyde.

The indicator reagent composition containing the diamino carboxylic acid can be used to generate a color response in the strip that correlates to the amount of glutaraldehyde present in the sample, and thereby quantitatively determine the glutaraldehyde concentration in a sample. The improved ability to differentiate a particular concentration of glutaraldehyde is an important advantage for identifying and quantifying the dialdehyde content in a sample, and is quite unexpected in light of the present state of the art.

In accordance with an important feature of the present invention, the continuing and substantial problems in dry phase test strips for quantitatively assaying a sample for high concentrations of dialdehydes are essentially eliminated. An indicator reagent composition of the present invention provides a differentiable response to the dialdehyde concentration over a range of 0% to about 20%, and particularly about 0.5% to about 6%, by weight of the sample. Therefore, accurate and reliable assays for dialdehyde content in undiluted samples can be performed by utilizing an indicator reagent composition and device of the present invention.

Modifications and variations of the invention as hereinbefore set forth can be made without departing from the spirit and scope thereof, and, therefore, only such limitations should be imposed as are indicated by the appended claims.

What is claimed is:

1. A composition comprising:
   (a) a diamino carboxylic acid in an amount of about 5% to about 25%, by weight of the composition, said diamino carboxylic acid is selected from the group consisting of lysine, ornithine, L-2,3-diaminopropionic acid, L-2,3-diaminobutyric acid, arginine, canavanine, hydroxylysine, asparagine, glutamine, and mixtures thereof;
   (b) a water-soluble polymer; and
   (c) a carrier comprising water.

2. The composition of claim 1 wherein the diamino carboxylic acid is lysine, ornithine, arginine, or a mixture thereof.

3. The composition of claim 1 wherein the diamino carboxylic acid is present in an amount of about 5% to about 15%, by weight of the composition.

4. The composition of claim 1 wherein the water-soluble polymer comprises a nonionic polymer.

5. The composition of claim 4 wherein the polymer comprises a cellulose-based polymer.

6. The composition of claim 5 wherein the cellulose-based polymer is selected from the group consisting of methylcellulose, hydroxymethylcellulose, hydroxyethylcellulose, hydroxyethylmethylcellulose, hydroxypropylcellulose, hydroxypropylmethylcellulose, carboxymethylcellulose and salts thereof, hydroxybutylcellulose, cellulose acetate, carboxymethylhydroxyethylcellulose, hydroxybutylmethylcellulose, and mixtures thereof.

7. The composition of claim 6 wherein the polymer comprises hydroxyethylcellulose.

8. The composition of claim 4 wherein the polymer is selected from the group consisting of polyvinylpyrrolidone, hydrolyzed polyvinylpyrrolidone, poly(vinyl alcohol), poly(vinyl acetate), vinyl acetate-vinyl alcohol copolymer, poly-(methacrylamide), a polyoxypropylene-polyoxyethylene block polymer having a structure:

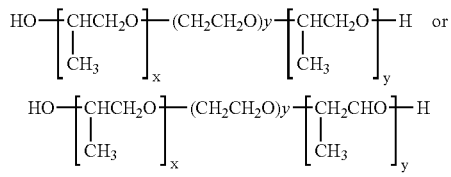

wherein x and z, independently, are an integer from about 4 to about 30, and y is an integer from about 4 to about 100, polyacrylamide, a vinyl alcohol copolymer, and mixtures thereof.

9. The composition of claim 4 wherein the polymer is present in an amount of 0.1% to about 5%, by weight of the composition.

10. The composition of claim 1 further comprising an anionic surfactant or a nonionic surfactant.

11. The composition of claim 10 wherein the anionic surfactant or nonionic surfactant is selected from the group consisting of an ethoxylated polysorbate, an ethoxylated alcohol, an ethoxylated phenol, a polyethylene glycol, a polypropylene glycol, an ethylene glycol-propylene glycol copolymer, an alkyl sulfate, an alkyl ether sulfate, an alkyl ether sulfonate, a sulfate ester of an alkylphenoxy polyoxyethylene ethanol, an alpha-olefin sulfonate, a beta-alkyloxy alkane sulfonate, an alkyl arylsulfonate, an alkyl carbonate, an alkyl ether carboxylate, a fatty acid, a sulfosuccinate, an alkyl ether sulfosuccinate, a sarcosinate, an octoxynol phosphate, a nonoxynol phosphate, a taurate, a fatty tauride, a sulfated monoglyceride, a fatty acid amido polyoxyethylene sulfate, and mixtures thereof.

12. The composition of claim 1 comprising:
   (a) about 5% to about 25% by weight diamino carboxylic acid; and
   (b) about 0.1% to about 5% by weight of hydroxypropylcellulose, hydroxyethylcellulose, methylcellulose, hydroxymethylcellulose, carboxymethylcellulose, polyvinylpyrrolidone, and mixtures thereof.

13. The composition of claim 1 wherein the carrier further comprises an organic solvent.

14. The composition of claim 13 wherein the organic solvent comprises methanol, ethanol, or acetone.

* * * * *